United States Patent [19]

Kleiner et al.

[11] Patent Number: 4,816,605

[45] Date of Patent: Mar. 28, 1989

[54] PROCESS FOR THE PREPARATION OF BIFUNCTIONAL TERTIARY AROMATIC PHOSPHINE OXIDES

[75] Inventors: Hans-Jerg Kleiner, Kronberg/Taunus; Erwin Weiss, Hofheim am Taunus, both of Fed. Rep. of Germany

[73] Assignee: Hoechst Aktiengesellschaft, Frankfurt am Main, Fed. Rep. of Germany

[21] Appl. No.: 905,687

[22] Filed: Sep. 9, 1986

Related U.S. Application Data

[63] Continuation-in-part of Ser. No. 756,326, Jul. 18, 1985, Pat. No. 4,670,601.

[30] Foreign Application Priority Data

Sep. 11, 1985 [DE] Fed. Rep. of Germany ....... 3532359

[51] Int. Cl.$^4$ .............................................. C07F 9/02
[52] U.S. Cl. ...................................................... 568/14
[58] Field of Search .......................................... 568/14

[56] References Cited

U.S. PATENT DOCUMENTS

| | | | |
|---|---|---|---|
| 3,988,368 | 10/1976 | Ura et al. .......................... | 568/14 X |
| 4,101,655 | 7/1978 | Sukman . | |
| 4,670,601 | 6/1987 | Kleiner et al. ........................ | 568/14 |
| 4,675,446 | 6/1987 | Weiss .................................... | 568/14 |

FOREIGN PATENT DOCUMENTS 1238024 11/1967 Fed. Rep. of Germany .
3203186 8/1983 Fed. Rep. of Germany .

OTHER PUBLICATIONS

Maier, L., Helv. Chim. Act 47, 120–132 (1964).
Aguiar et al, J. Org. Chem. 34, 3349–3352 (1969).

*Primary Examiner*—Paul F. Shaver

[57] ABSTRACT

Tertiary aromatic phosphine oxides of the formula

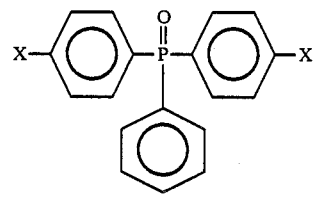

in which X=F, Cl or Br, are prepared by Friedel-Crafts reaction of
(a) phenylthiophosphonic dichloride with fluoro-, chloro-or bromobenzene, or
(b) of dichlorophenylphosphine, sulfur and fluoro-, chloro-or bromobenzene, and
(c) subsequent conversion of the phosphine sulfides produced by (a) or (b) using $H_2O_2$ in a solvent which comprises at least about 2% by weight, preferably at least about 10% by weight, of optionally halogenated lower aliphatic carboxylic acids and/or their anhydrides and, if appropriate, of other inert solvents which are miscible therewith.

The reaction products are final products and intermediates in various specialized fields, such as, for example, in the plant protection sector and the polymers sector.

20 Claims, No Drawings

PROCESS FOR THE PREPARATION OF BIFUNCTIONAL TERTIARY AROMATIC PHOSPHINE OXIDES

CROSS-REFERENCE TO RELATED APPLICATION

This application is a continuation-in-part of our copending application Ser. No. 756,326, filed Jul. 18, 1985, now U.S. Pat. No. 4,670,601, issued June 2, 1987.

Bifunctional tertiary aromatic phosphine oxides are, inter alia, the bis(4-halophenyl)phenylphosphine oxides of the formula

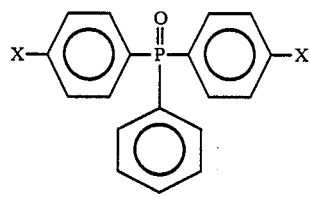

in which X = halogen.

They are valuable as final products and intermediates in various specialized fields, such as, for example, in the plant protection sector and in the polymers sector.

Bis(4-halophenyl)phenylphosphine oxides, for example, are final products in the plant protection sector as insecticides and acaricides (German Offenlegungsschrift No. 2,743,848 = U.S. Pat. No. 4,101,655).

The compounds are intermediate, for example, in the polymers sector, where the phosphine oxides are condensed with certain bisphenols to give valuable polymers (German Offenlegungsschrift No. 3,203,186), for example:

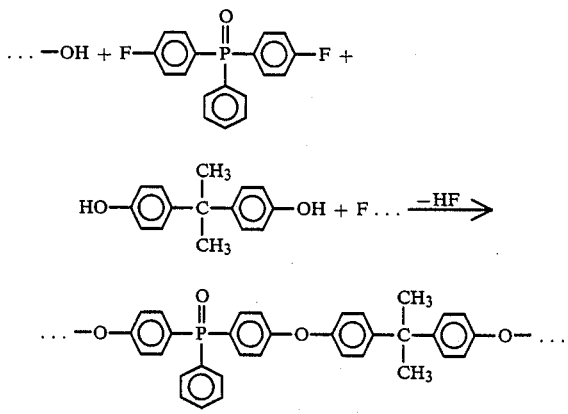

The polymers are distinguished by particular noncombustibility and extreme thermal stability; they can be processed to fibers, films and molded articles etc.

Bis(4-halophenyl)phenylphosphine oxides can—as stated in the previously mentioned German Offenlegungsschrift No. 2,743,848 - be prepared, for example, by Grignard reaction of dichlorophenylphosphine with halophenylmagnesium halide and subsequent oxidation, corresponding to the reaction equations below (schematic):

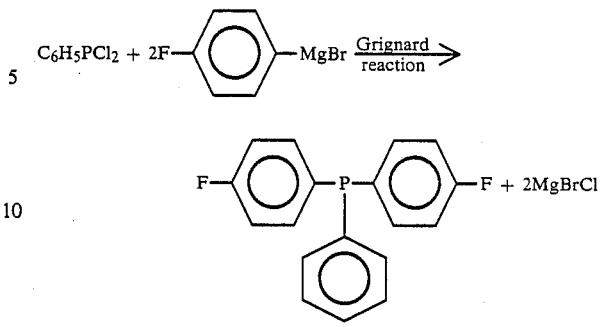

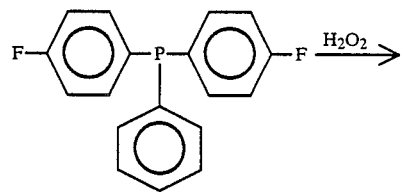

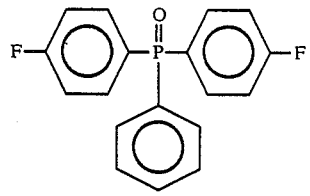

Alternatively, the phosphine oxides are obtained by Grignard reaction of phenylphosphonic dichloride with halophenylmagnesium halide:

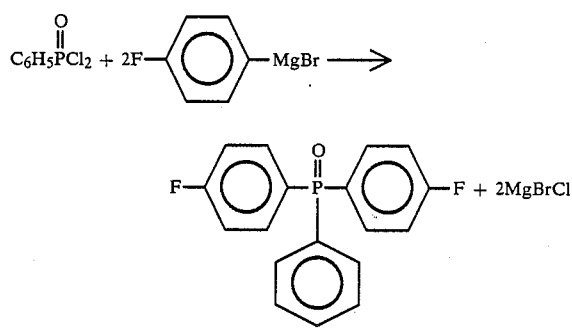

Finally, the preparation arylated thiophosphorus compounds, such as, for example, of bis(4-halophenyl)phenylphosphine sulfides, is also possible by the process of German patent No. 1,238,024, by Friedel-Crafts reaction of phosphorus thiohalide compounds, such as, for example, of phenylthiophosphonic dichloride $C_6H_5P(S)Cl_2$, with aromatic compounds, such as, for example, halobenzenes, in the presence of an at least equimolar amount, relative to the phosphorus thiohalide compound, of a Friedel-Crafts catalyst (particularly $AlCl_3$), and with an at least equimolar amount of the aromatic compounds, relative to the halogen atoms to be replaced, with subsequent decomposition of the catalyst complex compound which is produced using water, ice or, in a fashion which is known per se, by addition of a compound which forms a stronger complex with the catalyst than the thiophosphorus compound to be isolated. In the case, for example, of the preparation of bis(4-fluorophenyl)phenylphosphine sulfide by this process, the appropriate reaction equation would be:

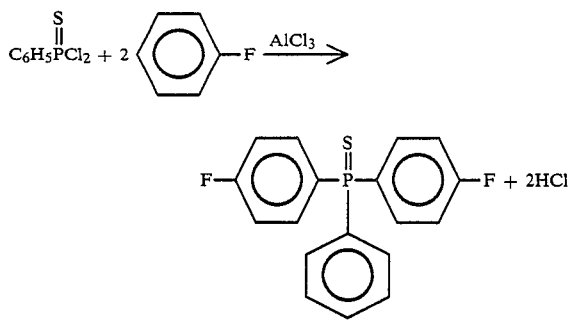

The preparation of this compound, and also of other bis(4-halophenyl)phenylphosphine sulfides, is, however, not supported by examples in the German patent mentioned.

The only examples which relate to the reaction with a halobenzene are Examples 7, 8 and 9 (reaction of $PSCl_3$ with chlorobenzene) and 15 and 16 (reaction of $PSCl_3$ with fluorobenzene).

According to Example 7, phosphorus thiochloride $PSCl_3$, $AlCl_3$ and chlorobenzene $C_6H_5Cl$ are refluxed for 7 hours in the molar ratio 1:5.33:6.67. The yield of tris(chlorophenyl)phosphine sulfide $PS(C_6H_4Cl)_3$ is stated as 64%, relative to $PSCl_3$ employed; according to the IR spectrum, the product is said to comprise approximately equal parts of the o- and p-isomers.

In Example 8, the $PSCl_3$:$AlCl_3$:$C_6H_5Cl$ molar ratio is 1:2:4. After refluxing for 1¼ hours, the following are said to have been obtained:
63.2% of bis(chlorophenyl)thiophosphinic chloride $(C_6H_4Cl)_2P(S)Cl$ (after recrystallization), and
a not inconsiderable amount of a residue which is said to have comprised a mixture of isomeric tris(chlorophenyl)phosphine sulfides $(C_6H_4Cl)_3PS$. In Example 9, the $PSCl_3$:$AlCl_3$:$C_6H_5Cl$ ratio was 1:2.5:1. After refluxing for 1 hour, the following are said to have been obtained:
45.4% of chlorophenylthiophosphonic dichloride $(C_6H_4Cl)P(S)Cl_2$,
19.7% of bis(chlorophenyl)thiophosphinic chloride $(C_6H_4Cl)_2P(S)Cl$ as a mixture of isomers, and
18.3% of tris(chlorophenyl)phosphine sulfide $(C_6H_4Cl)_3P(S)$.

Mention of mixtures of isomers is only made in the case of the product of Example 7, the residue of Example 8 and of the middle fraction of Example 9. However, it can hardly be imagined that the other chlorophenyl products were then to any extent isomerically pure. It can therefore certainly be presumed that all the reaction products are corresponding mixtures of isomers.

According to Example 15, $PSCl_3$, $AlCl_3$ and fluorobenzene $C_6H_5F$ in the molar ratio 1:5.33:6.67 were refluxed for 4 hours. 79.5% of virtually isomerically pure bis(4-fluorophenyl)thiophosphinic chloride $(C_6H_4F)_2P(S)Cl$ with only a trace of the o-isomer and a small residue are said to have been obtained.

In Example 16, the $PSCl_3$: $AlCl_3$:$C_6H_5F$ molar ratio was 1:2.2: 1.1. The result after refluxing for 1¾ hours was:
23.2% of virtually pure fluorophenylthiophosphonic dichloride $(C_6H_4F)P(S)Cl_2$,
14.2% of bis(fluorophenyl)thiophosphinic chloride $(C_6H_4F)_2P(S)Cl$ (without indication of the isomeric purity), and
a not entirely negligible amount of a brown residue.

The phosphine oxides which are necessary for the polymers industry could then be obtained from the phosphine sulfides by reaction, for example, with $SOCl_2$ or with oxidants such as $KMnO_4$ or $HNO_3$; cf., for instance, Helvetica Chimica Acta 47, p. 120–132 (1964), particularly p. 124/-/25 (1964).

In this literature citation, the following reaction equations are stated for the oxidation using the 3 reagents mentioned:

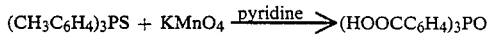

For the method using thionyl chloride $SOCl_2$, the strong corrosive action of this reagent and the formation of strongly smelling disulfur dichloride $S_2Cl_2$ is disadvantageous in this reaction.

The oxidation using $KMnO_4$ in pyridine without exception gives only moderate yields of phosphine oxide and proceeds —as can be seen from the reaction equation above with oxidation of the alkyl group located on the aromatic nucleus to the carboxyl group in the case of the use of nucleus-alkylated aromatic phosphine sulfides.

In the case of the reaction using concentrated nitric acid, a nitration of the aromatic nuclei present occurs simultaneously in addition to the formation of phosphine oxide.

A more favorable method for the oxidation of tertiary phosphine sulfides to the corresponding phosphine oxides is the hydrogen peroxide method published by A. M. Aguiar et al. in J. Org. Chem. 34, p. 3349–3352, particularly p. 3351, right-hand column, final paragraph (1969). The method was described with reference to the oxidation of dimethyl-1-butynylphosphine sulfide using an approximately 75% excess of $H_2O_2$ in methanol:

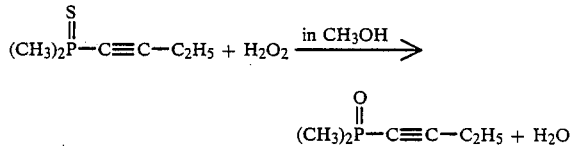

After allowing the batch to stand for two days and appropriate work-up, the yield of dimethyl-1-butynylphosphine oxide is said to have been 61%. This method is also not satisfactory because of the long reaction time, the only moderate yield, and also because of the necessity of working-up the hydrogen peroxide employed in excess.

The object was therefore to find an improved process for the preparation of bis(4-halophenyl)phenylphosphine oxides.

This object was achieved, according to the invention, by a further development of the process described in German patent No. 1,238,024 with conversion of the crude phosphine sulfides which are produced to the corresponding phosphine oxides.

The invention therefore relates to a process for the preparation of tertiary aromatic phosphine oxides of the formula

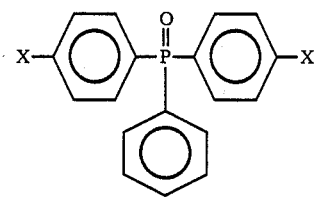

in which X=F, Cl or Br, by Friedel-Crafts reaction of phenylthiophosphonic chloride with a halobenzene, and subsequent conversion of the crude phosphine sulfides which are produced to the corresponding phosphine oxides by oxidative treatment with $H_2O_2$; the process comprises (a) heating phenylthiophosphonic dichloride with aluminum halide and a haloaromatic $C_6H_5X$, in which X has the abovementioned meaning, in the molar ratio 1:approximately (2-3.5): approximately (2-20) until the reaction is complete, or (b) heating dichlorophenylphosphine with a mixture of sulfur, aluminum halide and a haloaromatic $C_6H_5X$, in which X has the abovementioned meaning, in the molar ratio 1:approximately 1:approximately (2-3.5):approximately (2-20) until the reaction is complete, and (c) reacting the crude phosphine sulfides which are produced by (a) or (b), after hydrolytic work-up and, if appropriate, after removal of the excess haloaromatics by distillation, with hydrogen peroxide in a solvent which comprises at least about 2% by weight, preferably at least about 10% by weight, of—optionally halogenated—lower aliphatic carboxylic acids and/or of anhydrides and, if appropriate, furthermore of other inert solvents which are miscible with these.

The process stages (a), (b) and (c) are based on the following reaction equations:

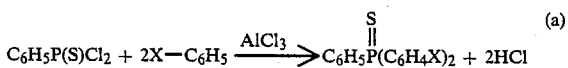

Bis(4-halophenyl)phenylphosphine sulfides are formed to a by far predominant extent by this process (both by version (a) and by version (b)), and they are converted to the corresponding phosphine oxides in virtually quantitative yields by the oxidation according to (c). The overall yields of phosphine oxides are in all cases between about 65 and 90% of theory, relative to the starting phosphorus component phenylthiophosphonic dichloride $C_6H_5P(S)Cl_2$ or dichlorophenylphosphine $C_6H_5PCl_2$, besides only relatively few isomers and other byproducts. This is surprising, above all because, at least in the case of the reaction with chlorobenzene, 64% of tris(chlorophenyl)phosphine sulfide which comprises approximately equal parts of o- and p-isomers, corresponding to an overall yield of about 32% of isomerically pure product, are obtained after 7 hours from $PSCl_3$, $AlCl_3$ and chlorobenzene in the molar ratio 1:5.33:6.67 according to German patent No. 1,238,024 (Example 7).

Furthermore, the reaction, according to Example 8 of German patent No. 1,238,024, of $PSCl_3$, $AlCl_3$ and chlorobenzene in the molar ratio 1:2:4 gives 63.2% of a mixture of approximately equal parts of o- and p-bis(chlorophenyl)thiophosphinic chloride after refluxing for 1¼ hours, corresponding to a yield of approximately 30-35% of theory, relative to the phosphorus component employed, of pure bis(4-chlorophenyl)thiophosphinic chloride. A similar distribution of isomers would also be expected for bis(chlorophenyl)phenylphosphine sulfide using the Friedel-Crafts reaction between phenylthiophosphonic chloride and chlorobenzene, or also for the corresponding oxide after oxidation according to sub-step (c). In fact, however, only up to a maximum of about 10% of the (2-chlorophenyl)(4-chlorophenyl)phenylphosphine oxide and (3-chlorophenyl)(4-chlorophenyl)phenylphosphine oxide isomers are detected by $^{31}P$ NMR and GC investigations besides 90.0-96% of bis(4-chlorophenyl)phenylphosphine oxide.

According to Example 15 of German Patent 1,238,024, $PSCl_3$, $AlCl_3$ and fluorobenzene $C_6H_5F$ in the molar ratio 1:5.33:6.67 are refluxed for 4 hours. 79.5% of theory of virtually isomerically pure bis(4-fluorophenyl)thiophosphinic chloride (4-F-$C_6H_4)_2P(S)Cl$ with only a trace of the o-isomer and a small residue are said to be obtained. Hardly any tertiary aromatic phosphine sulfides are formed, even in the molar ratio fluorobenzene/$PSCl_3$ of 6.67:1. Surprisingly, it has now been found that, using the process according to the invention, phenylthiophosphonic chloride, as such using version (a), or produced in the reaction mixture from dichlorophenylphosphine and sulfur in a type of one-pot reaction (since no intermediates are isolated) using version (b), can be arylated without difficulty to bis(4-fluorophenyl)phenylphosphine sulfide. 85% of theory (relative to the phosphorus component) of bis(4-fluorophenyl)phenylphosphine oxide are thus obtained by oxidation, according to process step (c), of the unpurified crude product obtained by version (b). This phosphine oxide must necessarily have previously been present as the phosphine sulfide.

$AlCl_3$, $AlBr_3$ and alkylaluminum chloride and bromide are preferably employed as aluminum halides for the process according to the invention; $AlCl_3$ is particularly preferred.

Fluoro-, chloro-, and bromobenzene are suitable as haloaromatic $C_6H_5X$, fluoro- and chlorobenzene being preferred.

The conversion, according to process stage (c), of the crude phosphine sulfides, prepared by (a) or (b), using hydrogen peroxide in lower aliphatic carboxylic acids and/or their anhydrides, if appropriate in the presence of a further inert solvent, proceeds in short reaction times, without formation of interferring byproducts, in quantitative or virtually quantitative yields to form the appropriate phosphine oxide. This is extremely surprising in view of the only moderate yield in the case of the oxidation using $H_2O_2$ in pure methanol (cf. A.M. Aguiar et al. in J. Org. Chem. 34, p. 3349 (1969)), and also—as our own experiments have shown—in view of the negative result obtained by treating tertiary phosphine sulfides with $H_2O_2$ in other solvents (acetonitrile, acetone etc.).

Aliphatic $C_1$-$C_6$-carboxylic acids, which can be further substituted by one or more halogen atoms, preferably F and/or Cl, are preferably suitable as optionally halosubstituted lower aliphatic carboxylic acids. Examples of such carboxylic acids are:

Formic acid
Acetic acid
Propionic acid
Monochloroacetic acid
Monofluoroacetic acid
Trifluoroacetic acid etc.

The carboxylic acids, and also their anhydrides, can be used both individually and also in mixtures with one another. They should comprise at least about 2% by weight, preferably at least about 10% by weight, of the total solvent.

It is particularly preferred when these carboxylic acids and/or their anhydrides are the only solvent. Acetic acid is very particularly preferably the only solvent.

If the carboxylic acids mentioned and/or their anhydrides are not employed as the only solvent, then the components of the mixture must be miscible with the carboxylic acids and/or their anhydrides; in addition, they may not, of course, react in an undesired fashion with the hydrogen peroxide or the starting materials and final products of the reaction. Suitable components of a mixture of this type are therefore, for example, water, lower ($C_1$-$C_6$)alcohols such as, for example, methanol, ethanol, n-propanol, i-propanol, n-butanol, i-butanol, tert.-butanol, cyclohexanol, etc., lower aliphatic halogenated hydrocarbons such as, for example, methylene chloride, 1,2-dichloroethane, etc., aromatic hydrocarbons such as, for example, toluene or xylene, and aromatic fluorohydrocarbons such as, for example, chlorobenzene, fluorobenzene etc.

Water and alcohols as components of the mixture are only appropriate in mixtures with the abovementioned carboxylic acids, not with their anhydrides, since they form the acids or esters with the anhydrides. If it is intended to use the acids as solvents, they are advantageously employed directly as such and not first produced from the anhydrides and water.

The less miscible the additional solvent components are with the carboxylic acids and/or their anhydrides, then, of course, the lower their proportion of the corresponding solvent mixture may be.

Hydrogen peroxide can be employed as an approximately 3 to 85% strength aqueous solution, expediently in a commercially available form (about 30–35% strength). The hydrogen peroxide is preferably used in an approximately equimolar amount, relative to the phosphorus sulfur compound. If further oxidizable contaminants are present, increased consumption of hydrogen peroxide is, of course, observed. Larger excesses are possible, but are no longer of advantage.

To carry out version (a) of the process according to the invention, phenylthiophosphonic dichloride, aluminum halide and haloaromatic are mixed in a suitable vessel, the molar ratio of the three reactants mentioned being 1:approximately (1–3.5):approximately (2–20), preferably 1: approximately (1–2.45):approximately (4–12).

Larger excesses of aluminum halide or haloaromatic are also possible, but are no longer of advantage.

Version b) of the process according to the invention starts from dichlorophenylphosphine, sulfur, aluminum halide and haloaromatic in the molar ratio 1:approximately 1:approximately (1–3.5):approximately (2–20), preferably 1:approximately 1:approximately (1–2.5):approximately (4–12). Here also, larger excesses of aluminum halide and haloaromatic are possible, but are no longer of advantage.

The fact that the—technically only controllable with difficulty—great heat of the reaction between dichlorophenylphosphine and sulfur is absorbed by the high heat capacity of the reaction materials without any dangerous increase in temperature has an advantageous effect in this case.

The further procedure in versions (a) and (b) of the process according to the invention is no longer different. The reaction mixture is now—preferably under reflux—heated until the reaction is complete. Reaction temperature is, in general, between about 70 and 150° C., and the reaction time is between about 4 and 70 hours.

It is expedient to heat the reaction mixture under an inert gas atmosphere (for example nitrogen or argon).

The end of the Friedel-Crafts reaction can be detected from the cessation of hydrogen chloride evolution (see the reaction equations) or by following the reaction progress in a conventional fashion (for example using chromatographic methods, particularly by means of $^{31}P$ NMR spectroscopy).

In both versions (a) and (b) of the process according to the invention, inert solvents—particularly to regulate the reaction temperature, when refluxing—can also be added. Such inert solvents can be, for example:

aliphatic hydrocarbons such as petroleum ether, hexane or octane; cycloaliphatic hydrocarbons such as cyclohexane, or hydroaromatics such as decalin, etc.

The Friedel-Crafts reaction mixture is worked-up by methods which are known in principle. Work-up always includes subsequent treatment with water. For example, the reaction solution—expediently with cooling—is introduced into water or poured onto granulated ice. To improve the phase separation, a suitable inert organic solvent can under certain circumstances be added—if not already present—the inert solvents previously mentioned or a further haloaromatic, methylene chloride, toluene, etc., being suitable.

The entire organic phase produced is—if necessary after further washing with water—subjected to distillation if solvent or excess haloaromatic are to be separated. The distillation residues produced during this substantially represent the bis(4-halophenyl)phenylphosphine sulfides desired. These can be fed to the oxidation stage (c) without further purification. For this, the phosphine sulfide is taken up in a solvent which comprises at least about 2% by weight of—optionally halogenated lower aliphatic carboxylic acids and/or their anhydrides, and the remainder of other inert solvents which are miscible therewith.

The phosphine sulfide to total solvent ratio can be varied within broad limits; the weight ratio is preferably about 1:(1–20). Hydrogen peroxide as an aqueous solution is metered into the solution or suspension at temperatures between about −5 and +100° C., preferably between about +40 and +80° C., or alternatively under reflux conditions when a high proportion of alcohol such as methanol (as solvent component) is used. Since the reaction proceeds exothermally, cooling may be necessary.

The end of the reaction can easily be determined by chromatographic or spectroscopic methods. When the crude phosphine sulfides are used, a slightly increased consumption of hydrogen peroxide—caused by oxidizable contaminants —is frequently detected.

The reaction mixture is worked-up, in a fashion which is known per se, by separation of the sulfur which is produced in elementary form from the cooled solution by filtration.

The very low solubility of elementary sulfur in carboxylic acids and/or their anhydrides, and also in mixtures thereof with other inert solvents which are miscible therewith—particularly in acetic acid/methanol mixtures —and also the very good solubility of tertiary phosphine oxides in these solvents or solvent mixtures—also in the presence of water unavoidably produced during the reaction—have a particularly favorable effect here.

After removal of the solvent by distillation (preferably in vacuo), the crude phosphine oxides remain.

The crude products are expediently further purified by stirring with water and washing acidic contaminants out using dilute alkaline solutions. The phosphine oxides frequently crystallize out during this in the form of their hydrates. These can be separated by filtration or—if they are liquid-separated as a second phase. Further purification is carried out in a fashion which is known per se by distillation or crystallization.

Because the reaction is simple to carry out, and because of the short reaction times and the high yields of phosphine oxide, the process represents a considerable advance in this area.

A further advance is that, in a multistage synthesis of this type, purification need only be carried out in the stage of the final product.

It should likewise be mentioned as an important advance that only an extremely small excess, if any, of hydrogen peroxide need be used during the oxidation using hydrogen peroxide according to the process according to the invention (in contrast to the process described by A. M. Aguiar et al. loco cit.), which considerably simplifies the work-up and is also very desirable for safety reasons.

The following examples are intended to describe the invention in greater detail:

EXAMPLE 1

Bis(4-fluorophenyl)phenylphosphine oxide (version a)

422.1 g (2 mol) of benzenethiophosphonic dichloride,
666.7 g (5 mol) of aluminum chloride and
1153.3 g (12 mol) of fluorobenzene
(Molar ratio 1:2.5:6)
were mixed with stirring under a nitrogen atmosphere. The mixture was then heated to reflux and refluxed for 18 hours. The reaction temperature at the end was 97° C. . The mixture was cooled and poured onto 5 kg of ice. The phases were separated and the aqueous phase was rinsed several times with 200 ml of chlorobenzene. The combined organic phases were freed of excess solvent in vacuo, and the oily residue was dissolved in 900 ml of acetic acid at 60° C. .
200 g of a 35% strength hydrogen peroxide solution (=2.06 mol; 3% excess) were added dropwise at this temperature in the course of 4 hours. Sulfur was separated by filtration and the filtrate was evaporated at a final temperature of 100° C. /20 mbar. The residue was taken up in
1000 g of chlorobenzene, and 2N NaOH was added until the solution was alkaline.

After separating the phases, the organic phase was rinsed several times with water and the solvent was stripped off in vacuo. 540 g of crude phosphine oxide were obtained, which were distilled in a high vacuum (b.p. 191° C. /0.1 mbar) and subsequently recrystallized from toluene/cyclohexane. 425 g (67.6% of theory) of pure bis(4-fluorophenyl)phenylphosphine oxide, m.p. 126°-127° C. , were obtained.

EXAMPLE 2

Bis(4-fluorophenyl)phenylphosphine oxide (version b)

268.5 g (1.5 mol) of dichlorophenylphosphine,
48.1 g (1.5 mol) of sulfur,
500 g (3.75 mol) of aluminum chloride and
865 g (9 mol) of fluorobenzene
(molar ratio 1:1:2.5:6)
were mixed under a protective gas atmosphere (sequence of addition: 1. AlCl$_3$, 2. sulfur, 3. fluorobenzene, 4. dichlorophenylphosphine), and, after the exothermic reaction had subsided,
300 ml of cyclohexane were added. The mixture was refluxed for 67 hours, cooled and introduced dropwise into 2 l of water at a maximum of 20° C. with external cooling. The phases were separated, the organic phase was washed several times with water and evaporated in vacuo, and the residue was dissolved in a mixture of
100 ml of glacial acetic acid/900 ml of methanol.
181 g of 35% strength hydrogen peroxide (25% excess) were added dropwise at 50° C. , the solution was stirred for 3 hours at 50° C. and cooled to 20° C. , sulfur was separated by filtration, and the filtrate was evaporated in vacuo. The residue which crystallized on cooling was dissolved in 500 ml of water by heating, treated with sodium hydroxide solution until alkaline, washed several times with water, and finally distilled. (b.p. 191° C. /0.1 mbar). 400 g of a virtually colorless, rapidly crystallizing oil were obtained which comprised, according to GC, to 92.96% of bis(4-fluorophenyl)phenylphosphine oxide. This corresponds to an overall yield of 78.9% of theory.

EXAMPLE 3

Bis(4-fluorophenyl)phenylphosphine oxide (version b)

357.98 g (2 mol) of dichlorophenylphosphine,
64.12 g (2 mol) of sulfur,
666.7 g (5 mol) of aluminum chloride and
1353.3 g (12 mol) of fluorobenzene
(molar ratio 1:1:2.5:6, sequence of addition: 1. AlCl$_3$, 2. sulfur, 3. fluorobenzene, 4. dichlorophenylphosphine)
were refluxed for 28 hours. Further work-up was carried out completely analogously to Example 1. After crystallization, 520.52 g of pure bis(4-fluorophenyl)phenylphosphine oxide were obtained (yield 82.8% of theory).

EXAMPLE 4

Bis(4-fluorophenyl)phenylphosphine oxide (version b)

357.97 g (2 mol) of dichlorophenylphosphine,
64.12 g (2 mol) of sulfur,
586.7 g (4.4 mol) of aluminum chloride and
1350.7 g (12 mol) of chlorobenzene
(molar ratio 1:1:2.2:6, sequence of addition: 1. AlCl₃, 2. sulfur, 3. chlorobenzene, 4. dichlorophenylphosphine)
were refluxed for 9 hours. The further work-up was carried out analogously to Example 1, but a distillation was not carried out. After crystallization from cyclohexane/toluene, 484 g of bis(4-fluorophenyl)-phenylphosphine oxide (m.p. 103°–105° C. ) were obtained; yield: 70% of theory.

EXAMPLE 5

Bis(4-fluorophenyl)phenylphosphine oxide (version b)

17.9 g (0.1 mol) of dichlorophenylphosphine,
3.2 g (0.1 mol) of sulfur,
29.3 g (0.22 mol) of aluminum chloride and
67.5 g (0.6 mol) of chlorobenzene
were refluxed for 7 hours. The work-up was carried out completely analogously to Example 1, but a bulb tube distillation was carried out here (oven temperature 225° C. /0.1 mbar). 30 g of a product with the isomeric distribution
88.7% of bis(4-chlorophenyl)phenylphosphine oxide,
6.2% and
3.6% of isomers, and
1.5% of impurities were obtained.
This corresponds to an overall yield of 76.6% of theory of the product desired.

EXAMPLE 6

Bis(4-chlorophenyl)phenylphosphine oxide (version b)

89.5 g (0.5 mol) of dichlorophenylphosphine,
16.03 g (0.5 mol) of sulfur,
220.1 g (1.65 mol) of aluminum chloride and
450 g (4 mol) of chlorobenzene
(molar ratio 1:1:3.3:8, sequence of addition: 1. AlCl₃, 2. sulfur, 3. chlorobenzene, 4. dichlorophenylphosphine)
were refluxed for 6.5 hours. After hydrolysis, separating the phases, drying over sodium sulfate and stripping of the solvent at 100° C. /0.5 mbar, the isomeric ratio of the phosphine sulfides produced were determined from the residue.
91.6% of bis(4-chlorophenyl)phenylphosphine sulfide,
7.9% of bis(chlorophenyl)phenylphosphine sulfide isomers and
0.5% of phenyl(4-chlorophenyl)thiophosphinic chloride
were found.
The further work-up was carried out analogously to Example 1 by reaction with 64.4 g of 35% strength hydrogen peroxide (33% excess) in 500 ml of glacial acetic acid. After filtration, stripping of the solvent and washing with alkali, 146 g of a product were obtained which, according to ³¹P NMR, comprised 94.4% of the bis(4-chlorophenyl)phenylphosphine oxide desired. This corresponds to an overall yield of 79.4% of theory.

We claim:

1. A process for the preparation of tertiary aromatic phosphine oxides of the formula

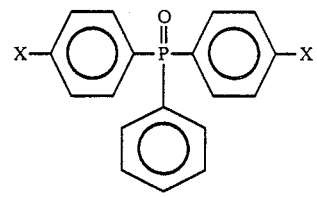

in which X=F, Cl and Br, which comprises heating phenylthiophosphonic dichloride with aluminum halide and haloaromatic C₆H₅X in which X has the above-mentioned meaning, in the molar ratio of 1:about (2–3.5) : about (2–20) until the reaction is complete, and reacting the crude phosphine sulfides thus produced, after hydrolytic work-up, with hydrogen peroxide in a solvent which comprises at least about 2% by weight of a lower aliphatic carboxylic acid or anhydride or halogenated lower aliphatic carboxylic acid or anhydride, or mixtures thereof.

2. The process as claimed in claim 1, wherein aluminum chloride AlCl₃ is used as aluminum halide.

3. The process as claimed in claim 1, wherein fluoro- or chlorobenzene is used as haloaromatic C₆H₅X.

4. The process as claimed in claim 1, wherein the heating is carried out at temperatures between about 70° C. and 150° C. until the reaction is complete.

5. The process as claimed in claim 1, wherein the oxidative treatment is carried out at temperatures between about −5° and +100° C.

6. The process as claimed in claim 1, wherein said reacting of the crude phosphine sulfides with hydrogen peroxide is carried out after hydrolytic work-up and after removal of excess haloaromatic by distillation.

7. The process as claimed in claim 1, wherein the reaction of the crude phosphine sulfides with the hydrogen peroxide is carried out in a solvent which comprises at least about 10% by weight of lower aliphatic carboxylic acids or anhydrides or halogenated lower aliphatic carboxylic acids or anhydrides or mixture thereof.

8. The process as claimed in claim 1, wherein the solvent additionally comprises other solvents, inert toward the reaction, which are miscible with said lower aliphatic carboxylic acids or anhydrides or halogenated lower aliphatic carboxylic acids or anhydrides.

9. The process as claimed in claim 7, wherein said reacting of the crude phosphine sulfides with hydrogen peroxide is carried out after hydrolytic work-up and after removal of excess haloaromatic by distillation.

10. The process as claimed claim 9, wherein the oxidative treatment is carried out at a temperature between about +40° and +80° C.

11. The process as claimed in claim 12, wherein the oxidative treatment is carried out at a temperature between about +40° and +80° C.

12. A process for the preparation of tertiary aromatic phosphine oxides of the formula

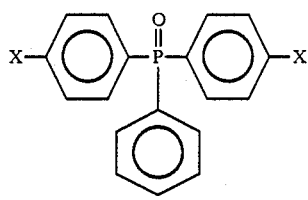

in which X=F, Cl and Br, which comprises heating dichlorophenylphosphine with a mixture of sulfur, aluminum halide and haloaromatic $C_6H_5X$ in which X has the abovementioned meaning, in the molar ratio 1:about 1:about (2-3.5) : about (2-20) until the reaction is complete, and reacting the crude phosphine sulfides thus produced, after hydrolytic work-up, with hydrogen peroxide in a solvent which comprises at least about 2% by weight of a lower aliphatic carboxylic acid or anhydride or halogenated lower aliphatic carboxylic acid or anhydride, or mixtures thereof.

13. The process as claimed in claim 12, wherein aluminum chloride $AlCl_3$ is used as aluminum halide.

14. The process as claimed in claim 12, wherein fluoro- or chlorobenzene is used as haloaromatic $C_6H_5X$.

15. The process as claimed in claim 12, wherein the heating is carried out at temperatures between about 70° C. and 150° C. until the reaction is complete.

16. The process as claimed in claim 12, wherein the oxidative treatment is carried out at temperatures between about −5° and +100° C.

17. The process as claimed in claim 12, wherein said reacting of the crude phosphine sulfides with hydrogen peroxide is carried out after hydrolytic work-up and after removal of excess haloaromatic by distillation.

18. The process as claimed in claim 12, wherein the reaction of the crude phosphine sulfides with the hydrogen peroxide is carried out in a solvent which comprises at least about 10% by weight of lower aliphatic carboxylic acids or anhydrides or halogenated lower aliphatic carboxylic acids or anhydrides or mixtures thereof.

19. The process as claimed in claim 12, wherein the solvent additionally comprises other solvents, inert toward the reaction, which are miscible with said lower aliphatic carboxylic acids or anhydrides or halogenated lower aliphatic carboxylic acids or anhydrides.

20. The process as claimed in claim 18, wherein said reacting of the crude phosphine sulfides with hydrogen peroxide is carried out after hydrolytic work-up and after removal of excess haloaromatic by distillation.

* * * * *

UNITED STATES PATENT AND TRADEMARK OFFICE
CERTIFICATE OF CORRECTION

PATENT NO. : 4,816,605
DATED : March 28, 1989
INVENTOR(S) : Hans-Jerg Kleiner, Erwin Weiss It is certified that error appears in the above-identified patent and that said Letters Patent is hereby corrected as shown below:

In column 2, line 51, insert --of-- between "preparation" and "arylated";

also line 51, "thiophos phorus" should read --thiophosphorus--.

In column 4, line 10, "124/-25" should read --124/125--.

In column 12, line 49 should read "...or anhydrides or mixtures thereof.".

Signed and Sealed this

Fifth Day of December, 1989

*Attest:*

JEFFREY M. SAMUELS

*Attesting Officer*   *Acting Commissioner of Patents and Trademarks*